US008277854B2

(12) United States Patent
Jouni et al.

(10) Patent No.: US 8,277,854 B2
(45) Date of Patent: Oct. 2, 2012

(54) NUTRITIONAL COMPOSITIONS CONTAINING PUNICALAGINS

(75) Inventors: Zeina Jouni, Evansville, IN (US); Deshanie Rai, Newburgh, IN (US); Nagendra Rangavajla, Dublin, OH (US)

(73) Assignee: Mead Johnson Nutrition Company, Evansville, IN (US)

( * ) Notice: Subject to any disclaimer, the term of this patent is extended or adjusted under 35 U.S.C. 154(b) by 91 days.

(21) Appl. No.: 12/915,308

(22) Filed: Oct. 29, 2010

(65) Prior Publication Data
US 2011/0045110 A1 Feb. 24, 2011

Related U.S. Application Data

(62) Division of application No. 12/471,750, filed on May 26, 2009, now abandoned.

(60) Provisional application No. 61/077,232, filed on Jul. 1, 2008.

(51) Int. Cl.
*A61K 36/00* (2006.01)
(52) U.S. Cl. ......... 424/777; 424/774; 424/776; 424/810
(58) Field of Classification Search ........................ None
See application file for complete search history.

(56) References Cited

U.S. PATENT DOCUMENTS

| 5,034,415 | A | 7/1991 | Rubin |
| 6,361,807 | B1 | 3/2002 | Aviram et al. |
| 6,375,993 | B1 | 4/2002 | Aviram et al. |
| 6,387,418 | B1 | 5/2002 | Aviram et al. |
| 6,929,793 | B2 | 8/2005 | Spivey-Krobath et al. |
| 6,989,161 | B2 | 1/2006 | Roufs et al. |
| 2002/0197341 | A1 | 12/2002 | Lansky |
| 2004/0131656 | A1 | 7/2004 | Roufs et al. |
| 2005/0058672 | A1* | 3/2005 | Gupta ........................... 424/401 |
| 2005/0118208 | A1 | 6/2005 | Bewert et al. |
| 2005/0118312 | A1 | 6/2005 | Lansky |
| 2005/0159483 | A1 | 7/2005 | Bassaganya-Riera |
| 2005/0165105 | A1 | 7/2005 | Bassaganya-Riera |
| 2005/0244518 | A1 | 11/2005 | Huang et al. |
| 2006/0211635 | A1 | 9/2006 | Seeram et al. |
| 2006/0251753 | A1 | 11/2006 | Alkayali |
| 2006/0269629 | A1 | 11/2006 | Bates et al. |
| 2006/0280819 | A1 | 12/2006 | Alkayali |
| 2007/0116839 | A1 | 5/2007 | Prakash et al. |
| 2008/0146664 | A1 | 6/2008 | Okuyama et al. |
| 2008/0214656 | A1* | 9/2008 | Lim et al. ..................... 514/450 |

FOREIGN PATENT DOCUMENTS

| EP | 1287825 | 4/2006 |
| WO | 2006121985 | 11/2006 |
| WO | 2006127832 | 11/2006 |

OTHER PUBLICATIONS

Agli, et al., "Antiplasmodial activity of *Punica granatum* L. fruit rind," Journal of Ethnopharmacology, 2009, pp. 1-7.

Ajaikumar, et al., "The inhibition of gastric mucosal injury by *Punica granatum* L (pomegranate) methanolic extract," Journal of Ethno-Pharmacology 96 (2005), pp. 171-176.
Albrecht, et al., "Redox active donor-substituted punicin derivatives," Org. Biomol. Chem., 2009, 7, pp. 1445-1453.
Arao, et al., "Dietary effect of pomegranate seed oil rich in 9cis, 11trans, 13cis conjugated linolenic acid on lipid metabolism in obese, hyperlipidemic OLETF Rats," Lipids in Health and Disease 2004, 3:24.
Aviram, et al., "Pomegranate Phenolics from the Peels, Arils, and Flowers Are Antiatherogenic: Studies in Vivo in Atherosclerotic Apolipoprotein E-Deficient (E0) Mice and in Vitro in Cultured Macrophages and Lipoproteins," J. Agric. Food Chem. 2008, 56, pp. 1148-1157.
Azmi, et al., "Resveratrol-Cu(ii) induced DNA breakage in human peripheral lymphocytes: Implications for anticancer properties," FEBS Letters 579 (2005) pp. 3131-3135.
Basu, et al., "Pomegranate juice: a heart-healthy fruit juice," Nutrition Reviews® vol. 67(1):49-56.
Berrin, et al., "Effect of drinks that are added as flavoring in oral midazolam premedication on sedation success," Pediatric Anesthesia 2008, 18, pp. 494-500.
Braga, et al., "Pomegranate extract inhibits *Staphy.ococcus aureus* growth and subsequent enterotoxin production," Journal of Ethnopharacology 96 (2005), pp. 335-339.
Cao, et al., "Re-characterization of three conjugated linolenic acid isomers by GC-MS and NMR," Chemistry and Physics of Lipids 145 (2007) pp. 128-133.
Cerdá, et al., "Evaluation of the bioavailability and metabolism in the rat of punicalagin, an antioxidant polyphenol from pomegranate juice," Eur. J. Nutr. (2003), 42, pp. 18-28.
Cuccioloni, et al., "Pomegranate fruit components modulate human thrombin," Fitoterapia 80 (2009) pp. 301-305.
Dept. of Health & Human Servcies, Memorandum, Subject: 75-Day Premarket Notification of New Dietary Ingredients.
Disilvestro, et al., "Pomegranate Extract Mouth Rinsing Effects on Saliva Measures Relevant to Gingivitis Risk," Phytother. Res. (2009).
Faria, et al., "Comment on Safety and Antioxidant Activity of a Pomegranate Ellagitannin-Enriched Polyphenol Dietary Supplement in Overweight Individuals with Increased Waist Size," J. Agric. Food Chem. 2008, 56, pp. 12143-12144.
Faria, et al., "Effect of pomegranate (*Punica granatum*) juice intake on hepatic oxidative street," Eur. J. Nutr. (2007), 46, pp. 271-278.
Fyfe, et al., "PAR-2 activation in intestinal epithelial cells potentiates interleukin-1 β-induced chemokine secretion via MAP kinase signaling pathways," Cytokine 31 (2005), pp. 358-367.
González-Sarrías, et al., "Dissimilar In Vitro and In Vivo Effects of Ellagic Acid and Its Microbiota-Derived Metabolites, Urolithins, on the Cytochrome P450 1A1," J. Agric. Food Chem. 2009, 57, pp. 5623-5632.
Gou, et al., "Evalution of Antioxidant Activity and Preventing DNA Damage Effect of Pomegranate Extracts by Chemiluminescence Method," J. Agric. Food Chem. 2007, 55, pp. 3134-3140.
Hadipour-Jahromy, et al., "Chondroprotective Effects of Pomegranate Juice on Monoiodoacetate-induced Osteoarthritis of the Knee Joint of Mice," Phytother. Res. (2009).
Halvorsen, et al., "A Systematic Screening of Total Anitoxidants in Dietary Plants," The Journal of Nutrition, 2002, pp. 461-471.

(Continued)

*Primary Examiner* — Christopher R. Tate
*Assistant Examiner* — Deborah A. Davis
(74) *Attorney, Agent, or Firm* — Waddey & Patterson, P.C.; James R. Cartiglia; Rebecca M. Barnett

(57) ABSTRACT

The present invention relates generally to a nutritional composition comprising punicalagins.

9 Claims, No Drawings

OTHER PUBLICATIONS

Hartman, et al., "Pomegranate juice decreases amyloid load and improves behavior in a mouse model of Alzheimer's disease," Neurobiology of Disease 24 (2006) pp. 506-515.

Hora, et al., "Chemopreventive Effects of Pomegranate Seed Oil on Skin Tumor Development in CD1 Mice," J. Med. Food 6 (3) 2003, pp. 157-161.

Hornung, et al., "Formation of conjugated $\Delta 11$ $\Delta 13$-doule bonds by $\Delta 12$-linoleic acid (1, 4)-acyl-lipid-desaturase in pomegranate seeds," Eur. J. Biochem. (2002) 269, pp. 4852-4859.

Huang, et al., "Pomegranate flower improves cardiac lipid metabolism in a diabetic rat model: role of lowering circulating lipids," British Journal of Pharmacology (2005) 145, pp. 767-774.

Jurenka, "Therapeutic Applications of Pomegranate (*Punica granatum* L.): A Review," Alternative Medicine Review, vol. 12, No. 2, 2008, pp. 128-144.

Khan, et al., "Oral Consumption of Pomegranate Fruit Extract Inhibits Growth and Progression of Primary Lung Tumors in Mice," Cancer Res 67: (7) 2007, pp. 3475-3482.

Kim, et al., "Stimulation of Osteoblastic Differentiation and Inhibition of Interleukin-6 and Nitric Oxide in MC3T3-E1 Cells by Pomegranate Ethanol Extract," Phytother. Res. (2009) 23, pp. 737-739.

Koba, et al., "Genetically Modified Rapeseed Oil Containing cis-9, trans-11, cis-13-Octadecatrienoic Acid Affects Body Fat Mass and Lipid Metabolism in Mice," J. Agric. Food Chem. 2007, 55 (9), pp. 3741-3748.

Kulkarni, et al., "In Vitro Studies on the Binding, Antioxidant, and Cytotoxic Actions of Punicalagin," J. Agric. Food Chem. 2007, 55, pp. 1491-1500.

Kumar-Roiné, et al., "Ability of certain plant extracts traditionally used to treat ciguatera fish poisoning to inhibit nitric oxide production in RAW 264.7 macrophages," Journal of Ethnopharmacology 123 (2009), pp. 369-377.

Lan, et al., "Transport behavior of ellagic acid of pomegranate leaf tannins and its correlation with total cholesterol alteration in HepG2 cells," Biomed. Chromatogr. 2009; 23: pp. 531-536.

Lansky, et al., "Pomegranate (*Punica granatum*) pure chemicals show possible synergistic inhibition of human PC-3 prostate cancer cell invasion across MatrigelTM," Investigational New Drugs 23: 2005 pp. 121-122.

Lansky, et al., "*Punica granatum* (pomegranate) and its potential for prevention and treatment of inflammation and cancer," Journal of Ethnopharmacology 109 (2007), pp. 177-206.

Larrosa, et al., "Anti-inflammatory properties of a pomegranate extract and its metabolite urolithin-A in a colitis rat model and the effect of colon inflammation on phenolic metabolism," Journal of Nutritional Biochemistry (2009), pp. 1-9.

Lawrence, et al., "Acetonitrile Covalent Adduct Chemical Ionization Mass Spectrometry for Double Bond Localization in Non-Methylene-Interrupted Polyene Fatty Acid Methyl Esters," Anal. Chem. 2006, 78, pp. 1312-1317.

Lei, et al., "Evidence of anti-obesity effects of the pomegranate leaf extract in high-fat diet induced obese mice," International Journal of Obesity (2007), 31, pp. 1023-1029.

Li, et al., "Pomegranate flower: a unique traditional antidiabetic medicine with dual PPAR-a/-y activator properties," Diabetes, Obesity and Metabolism, 10, 2008, pp. 10-17.

McCarrell, et al., "Antimicrobial activities of pomegranate rind extracts: enhancement by addition of metal salts and vitamin C," BioMed Central, BMC Complementary and Alternative Medicine, 2008, pp. 1-7.

Medeiros, et al., "Hemagglutinin residues of recent human A(H2N2) viruses that affect agglutination of chicken erythrocytes," International Congress Series 1219 (2001) pp. 369-374.

Mertens-Talcot, et al., "Absorbtion, Metabolism, and Antioxidant Effects of Pomegranate (*Punica granatum* L.) Polyphenols after Ingestion of a Standardized Extract in Healthy Human Volunteers," J. Agric. Food Chem. 2006, 54, pp. 8956-8961.
Naz, et al., "Antibacterial Activity Directed Isolation of Compounds from *Punica granatum*," Journal of Food Science, M: Food Microbiology & Safety, vol. 72, Nr. 9, 2007, pp. M341-M345.
Neurath, et al., "*Punica granatum* (Pomegranate) juice provides an HIV-I entry inhibitor and candidate topical microbicide," BMC Infectious Diseases 2004, 4:41.
Newton, et al., "The Herbal Alternatives for Menopause (HALT) Study: background and study design," Maturitas the European Menopause Journal, 52 (2005), pp. 134-146.
Okeke, "The Effects of Ellagic Acid on Insulin-like Growth Factor Binding Protein-2 in Human Prostate Cancer Cells," Graduate College of Bowling Green State University, Dec. 2006, p. 20, para 2, In 4-5; p. 39, In 12.
O'Shea, et al., "Immunomodulatory properties of conjugated linoleic acid1-3," Am J Clin Nutr 2004; 79(suppl) pp. 1199S-1206S.
Pacheco-Palencia, et al., "Protective Effects of Standardized Pomegranate (*Punica granatum* L.) Polyphenolic Extract in Ultraviolet-Irradiated Human Skin Fibroblasts," J. Agric. Food Chem. 2008, 56, pp. 8434-8441.
Patel, et al., "Safety assessment of pomegranate fruit extract: Acute and subchronic toxicity studies," Food and Chemcial Toxicology 46 (2008) pp. 2728-2735.
Rajfer, "Pomegranate Juice: Is It the New, All-Natural Phosphodiesterase Type 5 Inhibitor?" Rev Urol. 2008; 10(2); pp. 168-169.
Rasheed, et al., "Polyphenol-rich pomegranate fruit extract (POMx) suppresses PMACI-induced expression of pro-inflammatory cytokines by inhibiting the activiation of MAP Kinases and Nf-κB in human KU812 cells," Journal of Inflammation 2009, 6:1 pp. 1-12.
Ricci, et al., "Antioxidant activity of *Punica granatum* fruits," Fitoterapia 77 (2006) pp. 310-312.
Rivera, et al., "Long-term resveratrol administration reduces metabolic disturbances and lowers blood pressure in obese Zucker rats," Biochemical Pharmacology, 77 (2009), pp. 1053-1063.
Rock, et al., "Consumption of Wonderful Variety Pomegranate Juice and Extract by Diabetic Patients Increases Paraoxonase 2 Association with High-Density Lipoprotein and Stimulates Its Catalytic Activities," J. Agric. Food Chem. 2008, 56, pp. 8704-8713.
Seeram, et al., "Berry Fruits: Compositional Elements, Biochemical Activities, and the Impact of Their Intake on Human Health, Performance, and Disease," J. Agric. Food Chem. 2008, 56, pp. 627-629.
Seeram, et al., "Bioavailability of ellagic acid in human plasma after consumption of ellagitannins from pomegranate (*Punica granatum* L.) juice," Clinica Chimica Acta (2004) pp. 63-68.
Seeram, et al., "Comparison of Anitoxidant Potency of Commonly Consumed Polyphenol-Rich Beverages in the United States," J. Agric. Food Chem. 2008, 56, pp. 1415-1422.
Schubert, et al., "Antioxidant and eicosanoid enzyme inhibition properties of pomegranate seed oil and fermented juice flavonoids," Journal of Ethnopharmacology 66 (1999), pp. 11-17.
Tugcu et al., "Protective Effect of Potent Antioxidant, Pomegranate Juice, in the Kidney of Rats with Nephrolithiasis Induced by Ethylene Glycol," Journal of Endourolgoy vol. 22, No. 12, 2008, pp. 2723-2731.
Vasconcelos, et al., "Minimum Inhibitory Concentration of Adherence of *Punica granatum* Linn (pomegranate) Gel Against *S. mutans, S. mitis* and *C. albicans*," Braz Dent J (2006) 17(3): pp. 223-227.
Vincenzi, et al., "Anomalous electrophoretic behavior of a chitinase isoform from grape berries and wine in glycol chitin containing sodium dodecyl sulfate-polyacrylamide gel electrophoresis gels," Electrophoresis 2005, 26 pp. 60-63.
Wang, et al., "Bioactive Compounds from the Seeds of *Punica granatum* (Pomegranate)," J. Nat. Prod. 2004, 67, pp. 2096-2098.
Yamasaki, et al., "Dietary effect of pomegranate seed oil on immune function and lipid metabolism in mice," Nutrition 22, (2006) pp. 54-59.
Yoshimura, et al., "Inhibitory Effect of an Ellagic Acid-Rich Pomegranate Extract on Tyrosinase Activity and Ultraviolet-Induced Pigmentation," Biosci. Biotechnol. Biochem., 69 (12), 2005, pp. 2368-2373.

* cited by examiner

NUTRITIONAL COMPOSITIONS CONTAINING PUNICALAGINS

CROSS REFERENCE TO RELATED APPLICATIONS

This application is a divisional application which claims priority to commonly assigned U.S. patent application Ser. No. 12/471,750, filed May 26, 2009 now abandoned, which claims priority to U.S. Provisional Application No. 61/077,232, filed Jul. 1, 2008, the disclosures of which are incorporated herein by reference in their entirety.

BACKGROUND OF THE INVENTION

Field of the Invention

The present invention relates generally to nutritional compositions comprising punicalagins and methods of using nutritional compositions comprising punicalagins.

SUMMARY OF THE INVENTION

In an embodiment, the present invention is directed to nutritional compositions comprising a protein source, a fat source, a carbohydrate source, and punicalagins.

In another embodiment, the invention is directed to a method for enhancing the immune system in a pediatric subject via the administration of punicalagins.

Further, the invention, in an embodiment, is directed to a method for reducing allergic inflammatory responses in a pediatric subject via administration of punicalagins.

DETAILED DESCRIPTION OF THE PREFERRED EMBODIMENTS

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The present invention is directed, in some embodiments, to nutritional compositions comprising a protein source, a fat source, a carbohydrate source, and punicalagins. The nutritional composition may be provided in any form known in the art, such as a powder, a gel, a suspension, a paste, a solid, a liquid, a liquid concentrate, or a ready-to-use product. The nutritional composition may, in certain embodiments, comprise a nutritional supplement, children's nutritional product, infant formula, human milk fortifier, or any other nutritional composition designed for children or infants. As used herein, the terms "children" or "child" refer to human subjects between the ages of one and 13 years old. In some embodiments, the terms "children" or "child" refer to human subjects that are two, three, four, five, or six years old. The term "children's nutritional product" means a composition that satisfies at least a portion of the nutrient requirements of a child. As used herein, the term "infant" means a postnatal human that is less than about one year of age. The term "infant formula" means a composition that satisfies the nutrient requirements of an infant by being a substitute for human milk.

Punicalagins are tannins, which are large polyphenol compounds that are isomers of 2,3-(S)-hexahydroxydiphenoyl-4,6-(S,S)-gallagyl-D-glucose, hydrolysable tannins with a molecular weight of 1084. Punicalagins are the predominant pomegranate tannin.

In some embodiments of the invention, punicalagins are present in a nutritional composition in an amount ranging from about 0.004 to about 0.20 mg/g of the composition. In other embodiments of the invention, punicalagins are present in an amount ranging from about 0.008 to about 0.12 mg/g of the composition.

If the composition of the invention is administered to an infant or child, an amount of punicalagins ranging from about 1 mg to about 100 mg per day may be administered. In other embodiments, the amount of punicalagins administered to an infant or child via the composition of the invention may range from about 5 mg to about 50 mg per day. In some embodiments the amount of punicalagins administered to an infant or child via the composition of the invention may range from about 10 mg to about 35 mg per day.

In some embodiments, the nutritional composition of the present invention further comprises punicic acid. Punicic acid is a polyunsaturated fatty acid, 18:3 (n-5). It is obtained from pomegranate seed oil. Its chemical formula is $C_{18}H_{30}O_2$. Punicic acid is a conjugated linolenic acid. It has three conjugated double bonds, and it is chemically similar to the conjugated linoleic acids, which have two.

The term "punicic acid," as used herein, refers to a conjugated linolenic acid isomer containing cis-9, trans-11, cis-13 double bonds in the $C_{18}$ carbon chain, its non-toxic salts, active esters, active isomers, active metabolites, structural lipids containing punicic acid, and mixtures thereof.

In some embodiments of the invention, punicic acid is present in an amount ranging from about 0.01 to about 40 mg/g of the composition. In further embodiments of the invention, punicic acid is present in an amount ranging from about 0.02 to about 20 mg/g of the composition.

If the composition of the invention is administered to an infant or child, an amount of punicic acid ranging from about 25 mg to about 10 g per day may be administered. In further embodiments, the amount of punicic acid administered to an infant or child via the composition of the invention may range from about 50 mg to about 5 g per day.

If punicic acid is added to the nutritional composition of the present invention, the weight ratio of punicalagins:punicic acid may be from about 1:10,000 to about 4:1. In some embodiments of the present invention, the weight ratio of punicalagins:punicic acid may be from about 1:1,000 to about 1:1. In further embodiments, the ratio may be from about 1:500 to about 2:3.

In additional embodiments of the invention, the nutritional composition may further comprise pomegranate leaf extract. Although previous research has focused on the pomegranate fruit, the extract from pomegranate leaves may also provide health benefits. The use of pomegranate leaf extract in combination with punicalagins in accordance with the present invention may provide increased levels of health benefits in infants, children and adult mammal subjects.

In some embodiments of the invention, pomegranate leaf extract is present in an amount ranging from about 4 mg/g to about 60 mg/g of the composition. In further embodiments of the invention, pomegranate leaf extract is present in an amount ranging from about 12 mg/g to about 48 mg/g of the composition.

If the composition of the invention is administered to an infant or child, an amount of pomegranate leaf extract ranging from about 1 g to about 15 g per day may be administered. In further embodiments, the amount of pomegranate leaf extract administered to an infant or child via the composition of the invention may range from about 3 g to about 12 g per day. In some embodiments, the amount of pomegranate leaf extract administered to an infant or child via the composition of the invention may range from about 5 g to about 10 g per day.

If the nutritional composition contains pomegranate leaf extract, the weight ratio of punicalagins:pomegranate leaf extract may be from about 1:15,000 to about 1:100. In some embodiments of the present invention, the weight ratio of punicalagins:pomegranate leaf extract may be from about 1:2,400 to about 1:60. In further embodiments, the ratio may be from about 1:500 to about 1:10.

In further embodiments, the nutritional composition of the present invention contemplates the use of punicalagins with punicic acid and pomegranate leaf extract. The combination of punicalagins, punicic acid, and pomegranate leaf extract may provide increased levels of health benefits in infants, children, and adult mammal subjects.

If punicalagins are provided in an infant formula or children's nutritional product, the formula or product may be nutritionally complete and may contain suitable types and amounts of lipid, carbohydrate, protein, vitamins, and minerals. As used herein, the term "nutritionally complete" refers to a nutritional composition that may be used as the sole source of nutrition, which would supply to a subject essentially all the required daily amounts of vitamins, minerals, and/or trace elements in combination with the proteins, carbohydrates, and lipids.

If the composition of the present invention is provided as an infant formula, the amount of lipid or fat in an infant formula can vary from about 3 to about 7 g/100 kcal. Lipid sources can be any used in the art, e.g., vegetable oils such as palm oil, canola oil, corn oil, soybean oil, palmolein, coconut oil, medium chain triglyceride oil, high oleic sunflower oil, high oleic safflower oil, fish oil, and the like. The amount of carbohydrate can vary from about 8 to about 12 g/100 kcal. Carbohydrate sources can be any used in the art, e.g., lactose, glucose, corn syrup solids, maltodextrins, sucrose, starch, rice syrup solids, and the like.

The amount of protein, if the present composition is provided as an infant formula, can vary from about 1 to about 5 g/100 kcal. Protein sources can be any used in the art, e.g., nonfat milk, whey protein, casein, soy protein, hydrolyzed protein, amino acids, and the like. In a particular embodiment, the protein source contains both bovine whey and bovine casein. In an embodiment, the whey may be a denatured whey protein concentrate. In another embodiment, the whey may be an undenatured whey protein concentrate. In a specific embodiment, the protein source may contain both a denatured and an undenatured whey protein concentrate.

If the composition of the present invention is provided as an infant formula, suitable examples of infant formulas may include soy based, partially or extensively hydrolyzed, lactose-free, low-lactose, elemental, protein-free, anti-regurgitation, premature, or standard infant formulas. The type of infant formula used may be based on the needs of the infant for proper digestion and health.

The composition of the present invention may be provided to both term and preterm infants. As a result, if the composition of the present invention is provided as an infant formula, the infant formula may be a term infant formula or a preterm infant formula. Similarly, if the composition of the present invention is provided as a human milk fortifier, the human milk fortifier may be a term human milk fortifier or a preterm human milk fortifier.

Long chain polyunsaturated fatty acids (LCPUFA) have been shown to be important in infant development. Arachidonic acid (ARA; C20:4, n-6) and docosahexaenoic acid (DHA; C22:6 n-3) are of particular interest due to the high concentrations of each found in the infant brain and retina. ARA and DHA are synthesized from their respective 18 carbon precursors, linoleic acid (18:2, n-6) and α-linolenic acid (18:3, n-3) through alternate desaturation and elongation. DHA and ARA are typically obtained through breast milk in infants that are breast-fed. In infants that are formula-fed, however, DHA and ARA must be supplemented into the diet.

Evidence indicates that infants with altered LCPUFA levels, resulting from inadequate intake of dietary LCPUFA, may be at risk for neurological problems, may score lower on cognitive tests, and have lower retinal development than infants fed human milk. Thus, the provision of LCPUFA, in particular ARA and DHA, in amounts closely approximating those found in human milk may support adequate growth as well as neurological development in formula-fed infants. Thus, in some embodiments of the invention, the nutritional composition contains at least one LCPUFA. In a particular embodiment, the nutritional composition contains DHA and/or ARA.

If added to a nutritional composition, the weight ratio of ARA:DHA may be from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In other embodiments, the ratio is about 1:1.9. In a particular embodiment, the ratio is about 1.5:1. In a further embodiment, the ratio is about 1.47:1.

If DHA is included in the invention, the level of DHA may be between about 0.0% and 1.00% of fatty acids, by weight. In other embodiments, the level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

If ARA is included in the invention, the level of ARA may be between 0.0% and 0.67% of fatty acids, by weight. In another embodiment, the level of ARA may be about 0.67% by weight. In another embodiment, the level of ARA may be about 0.5% by weight. In yet another embodiment, the level of DHA may be between about 0.47% and 0.48% by weight.

If used, the amount of DHA in the present invention may be from about 2 mg/100 kilocalories (kcal) to about 100 mg/100 kcal. In another embodiment, the amount of DHA may be from about 5 mg/100 kcal to about 75 mg/100 kcal. In yet another embodiment, the amount of DHA may be from about 15 mg/100 kcal to about 60 mg/100 kcal.

If used, the amount of ARA in the present invention may be from about 4 mg/100 kilocalories (kcal) to about 100 mg/100 kcal. In another embodiment, the amount of ARA may be from about 10 mg/100 kcal to about 67 mg/100 kcal. In yet another embodiment, the amount of ARA may be from about 20 mg/100 kcal to about 50 mg/100 kcal. In a particular embodiment, the amount of ARA may be from about 25 mg/100 kcal to about 40 mg/100 kcal. In one embodiment, the amount of ARA is about 30 mg/100 kcal.

If the composition of the invention is supplemented with oils containing DHA and/or ARA, it may be accomplished using standard techniques known in the art. For example, an equivalent amount of an oil which is normally present in the composition may be replaced with DHA and/or ARA.

If utilized, the source of one or more of the LCPUFA can be any source known in the art such as marine oil, fish oil, single cell oil, egg yolk lipid, brain lipid, and the like. Any LCPUFA can be in natural form, provided that the remainder of the LCPUFA source does not result in any substantial deleterious effect on an infant or child. Alternatively, a LCPUFA can be used in refined form.

If used, the LCPUFA source may or may not contain eicosapentaenoic acid (EPA). In some embodiments, especially for feeding to infants the LCPUFA used in the invention contains little or no EPA. For example, in certain embodiments that the nutritional compositions used herein contain less than about 20 mg/100 kcal EPA; in some embodiments less than about 10 mg/100 kcal EPA; in other embodiments less than about 5 mg/100 kcal EPA; and in still other embodiments substantially no EPA.

In some embodiments of the invention, the nutritional composition contains additional components which may include probiotics or prebiotics. The term "probiotic" means a microorganism that exerts beneficial effects on the health of the host. Any probiotic known in the art may be added, provided it is suitable for combination with the other components of the composition. For example, the probiotic may be chosen from the group consisting of *Lactobacillus* and *Bifidobacterium*. Alternatively, the probiotic can be *Lactobacillus rhamnosus* GG.

In certain embodiments, the nutritional composition of the present invention additionally comprises at least one prebiotic. The term "prebiotic", as used herein, means a non-digestible food ingredient that stimulates the growth and/or activity of probiotics. In this embodiment, any prebiotic known in the art may be added, provided it is suitable for combination with the other components of the composition. In a particular embodiment, the prebiotic can be selected from the group consisting of fructo-oligosaccharide, inulin, gluco-oligosaccharide, galacto-oligosaccharide, isomalto-oligosaccharide, xylo-oligosaccharide, soybean oligosaccharides, chito-oligosaccharide, gentio-oligosaccharide, manno-oligosaccharide, lactulose, lactosucrose, raffinose, aribino-oligosaccharide, glucans, siallyl-oligosaccharide, polydextrose, inulin, fuco-oligosaccharide, and mixtures thereof.

In some embodiments, the use of punicalagins alone, or in combination with punicic acid or pomegranate leaf extract, or the combination of all three aid in immune system development and function in pediatric subjects. For example, the use of punicalagins alone, or in combination with punicic acid or pomegranate leaf extract, or the combination of all three may enhance resistance to infection and/or reduce allergic inflammatory responses including, but not limited to asthma, wheezing, atopic cough, bronchiolitis, bronchitis, and eczema. Thus, in some embodiments, the invention is directed to a method for enhancing the immune response in a pediatric subject comprising administering the nutritional composition of the present invention to the pediatric subject. In further embodiments, the invention is directed to a method for enhancing resistance to infection in a pediatric subject comprising administering the nutritional composition of the present invention to the pediatric subject. In other embodiments, the invention is directed to a method for reducing allergic inflammatory responses in a pediatric subject comprising administering the nutritional composition of the present invention to the pediatric subject. As used herein, the term "pediatric subject" refers to human subjects that are less than 13 years old. In some embodiments, the term "pediatric subject" refers to human subjects that are less than 8 years old.

Further, in some embodiments, the use of punicalagins alone or in combination with punicic acid, or pomegranate leaf extract, or the combination of all three may aid in enhancing cardiovascular health, eye health, brain development and function, gastrointestinal health and function. Further, the use of punicalagins alone, or in combination with punicic acid or pomegranate leaf extract, or the combination of all three may aid in reducing the risk of inflammation, cancer, or the metabolic syndrome, including obesity and diabetes mellitus. Thus, in some embodiments, the invention is directed to a method for enhancing cardiovascular health, and eye health in a pediatric subject by administering the nutritional composition of the present invention to the pediatric subject. In further embodiments the invention is directed to a method for enhancing brain development and function in a pediatric subject by administering the nutritional composition of the present invention to the pediatric subject. In other embodiments the invention is directed to a method of improving gastrointestinal health and function in a pediatric subject by administering the nutritional composition of the present invention to the pediatric subject. Such an embodiment of the invention could include providing a healthy intestinal micro flora balance in the pediatric subject. In some embodiments, the invention is directed to a method for reducing the risk of inflammation and cancer in a pediatric subject by administering the nutritional composition of the present invention to the pediatric subject. In further embodiments, the invention is directed to a method for reducing the risk of metabolic syndrome in a pediatric subject by administering the nutritional composition of the present invention to the pediatric subject. In such an embodiment, the reduction of the risk of metabolic syndrome in pediatric subjects could include reduction in the risk of obesity and diabetes mellitus.

In certain embodiments, the combination of punicalagins with punicic acid or with pomegranate leaf extract, or the combination of all three provides an enhanced effect with respect to the health benefits listed above. It is believed that the activity of the combination of punicalagins with punicic acid or with pomegranate leaf extract, or the combination of all three is greater than the added activity expected when each of the compounds are administered separately.

The following example describes an embodiment of the present invention. Other embodiments within the scope of the claims herein will be apparent to one skilled in the art from the consideration of the specification or practice of the invention disclosed herein. It is intended that the specification, together with the example, be considered to be exemplary only, with the scope of the invention being indicated by the claims which follow the example.

Example 1

Table 1 illustrates the nutrient components of one infant formula embodiment of a nutritional composition of the present invention.

TABLE 1

| (Normal Dilution) | Per 100 Calories (5 fl oz) | Per 100 grams Powder |
|---|---|---|
| Protein, g | 2.1 | 10.8 |
| Fat, g | 5.3 | 27 |
| Linoleic acid, mg | 860 | 4400 |
| Linolenic acid, mg | 85 | 440 |
| DHA, mg | 17 | 88 |
| ARA, mg | 34 | 175 |
| Carbohydrate, g | 10.9 | 56 |
| Water, g | 134 | 3.3 |
| Punicalagins, mg | 1.9 | 10 |
| Vitamins/Other Nutrients | | |
| Vitamin A, IU | 300 | 1550 |
| Vitamin D, IU | 60 | 310 |
| Vitamin E, IU | 2 | 10.3 |
| Vitamin K, mcg | 8 | 41 |
| Thiamin (Vitamin B1), mcg | 80 | 410 |
| Riboflavin (Vitamin B2), mcg | 140 | 720 |
| Vitamin B6, mcg | 60 | 310 |
| Vitamin B12, mcg | 0.3 | 1.55 |
| Niacin, mcg | 1000 | 5200 |
| Folic acid (Folacin), mcg | 16 | 83 |
| Pantothenic acid, mcg | 500 | 2600 |
| Biotin, mcg | 3 | 15.5 |
| Vitamin C (Ascorbic acid), mg | 12 | 62 |
| Choline, mg | 24 | 124 |
| Inositol, mg | 6 | 31 |
| Carnitine, mg | 2 | 10.3 |
| Taurine, mg | 6 | 31 |
| Minerals | | |
| Calcium, mg | 78 | 400 |
| Phosphorus, mg | 43 | 220 |
| Magnesium, mg | 8 | 41 |
| Iron, mg | 1.8 | 9.3 |
| Zinc, mg | 1 | 5.2 |
| Manganese, mcg | 15 | 77 |
| Copper, mcg | 75 | 390 |
| Iodine, mcg | 10 | 52 |
| Selenium, mcg | 2.8 | 14.5 |
| Sodium, mg | 27 | 139 |
| Potassium, mg | 108 | 560 |
| Chloride, mg | 63 | 330 |
| Molybdenum, mcg | NA | NA |
| Chromium, mcg | NA | NA |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the scope of the appended claims should not be limited to the description of the preferred versions contained therein.

What is claimed is:

1. A method of enhancing infection resistance in a pediatric subject comprising administering a nutritionally complete composition comprising punicalagins, punicic acid, and pomegranate leaf extract to the pediatric subject; wherein the amount of punicalagins administered is between about 1 mg to about 100 mg per day, the amount of punicic acid administered is between about 50 mg to about 5 g per day, and the amount of pomegranate leaf extract administered is between about 1 g to about 15 g per day.

2. The method according to claim 1, wherein the punicalagins are administered in a nutritional composition that further comprises a protein source, a fat source, and a carbohydrate source.

3. The method according to claim 1, wherein the pediatric subject is an infant.

4. A method of enhancing the immune system of a pediatric subject comprising administering a nutritionally complete composition comprising punicalagins, punicic acid, and pomegranate leaf extract to the pediatric subject; wherein the amount of punicalagins administered is between about 1 mg to about 100 mg per day, the amount of punicic acid administered is between about 50 mg to about 5 g per day, and the amount of pomegranate leaf extract administered is between about 1 g to about 15 g per day.

5. The method according to claim 4, wherein the punicalagins are administered in a nutritional composition that further comprises a protein source, a fat source, and a carbohydrate source.

6. The method according to claim 4, wherein the pediatric subject is an infant.

7. A method of enhancing infection resistance in a pediatric subject comprising administering a nutritionally complete composition comprising punicalagins, punicic acid, and pomegranate leaf extract to the pediatric subject; wherein the amount of punicalagins administered is between about 1 mg to about 100 mg per day, the amount of punicic acid administered is between about 50 mg to about 5 g per day, and the amount of pomegranate leaf extract administered is between about 1 g to about 15 g per day.

8. The method according to claim 7, wherein the punicalagins are administered in a nutritional composition that further comprises a protein source, a fat source, and a carbohydrate source.

9. The method according to claim 7, wherein the pediatric subject is an infant.

* * * * *